US006492641B1

United States Patent
Dep et al.

(10) Patent No.: US 6,492,641 B1
(45) Date of Patent: Dec. 10, 2002

(54) APPARATUS AND METHOD FOR GAMMA-RAY DETERMINATION OF BULK DENSITY OF SAMPLES

(75) Inventors: W. Linus Dep, Chapel Hill, NC (US); Robert E. Troxler, Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 63 days.

(21) Appl. No.: 09/606,645

(22) Filed: Jun. 29, 2000

(51) Int. Cl.[7] ............................................... G01N 23/06
(52) U.S. Cl. .................. 250/358.1; 250/255; 250/269.3; 378/54; 378/56
(58) Field of Search .................. 378/56, 54; 250/358.1, 250/255, 269.3

(56) References Cited

U.S. PATENT DOCUMENTS

| 3,393,313 A | * | 7/1968 | Harwick | ....................... 250/308 |
| 3,523,186 A | * | 8/1970 | Cohn et al. | ....................... 378/52 |
| 5,151,601 A | | 9/1992 | Regimand | |

OTHER PUBLICATIONS

Siew–Ann Tan and Tien–Fang Fwa; "Nondestructive Density Measurements of Cylindrical Specimens by Gamma–Ray Attenuation"; *Journal of Testing and Evaluation, JTEVA*; Mar. 1991; pp. 155–160; vol. 19, No. 2.

* cited by examiner

*Primary Examiner*—Constantine Hannaher
(74) *Attorney, Agent, or Firm*—Alston & Bird LLP

(57) ABSTRACT

A nuclear density gauge and test method is provided for measuring bulk density, especially of a cylindrically shaped sample such as asphalt paving material. The gauge comprises a base; a sample holder carried by the base and having a surface configured for receiving and holding a first generally planar end of the cylindrically shaped sample; a plate mounted in proximity to said sample holder; and at least three sources of gamma radiation located in said plate adjacent the sample holder. The sources are positioned in spaced-apart relation from one another for emitting gamma radiation from at least three spaced-apart locations into said one end of the sample. Each of the sources comprises an isotope having a characteristic primary energy. A detector is mounted to the base and is positioned adjacent the opposite end of the cylindrically shaped sample for receiving gamma radiation which has penetrated the sample. Means is provided cooperating with the detector for calculating the bulk density of the sample based upon the gamma radiation counts by the detector. Preferably the detector comprises a scintillation detector, and the means for calculating the bulk density of the sample includes an analyzer connected to the scintillation detector for detecting gamma radiation in a predetermined energy spectrum, which preferably falls within the range of 0.1 MeV to 2 MeV.

36 Claims, 7 Drawing Sheets

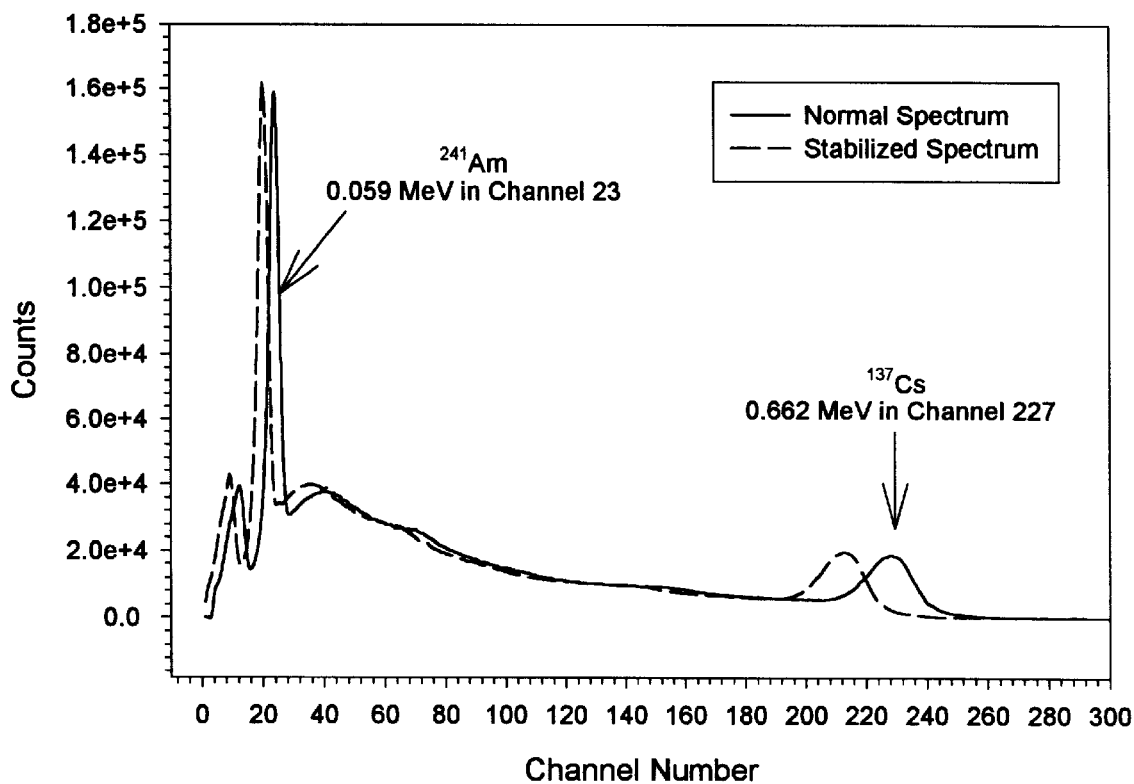
Figure 4 Normal and Stabilized Spectra of an Asphalt Sample

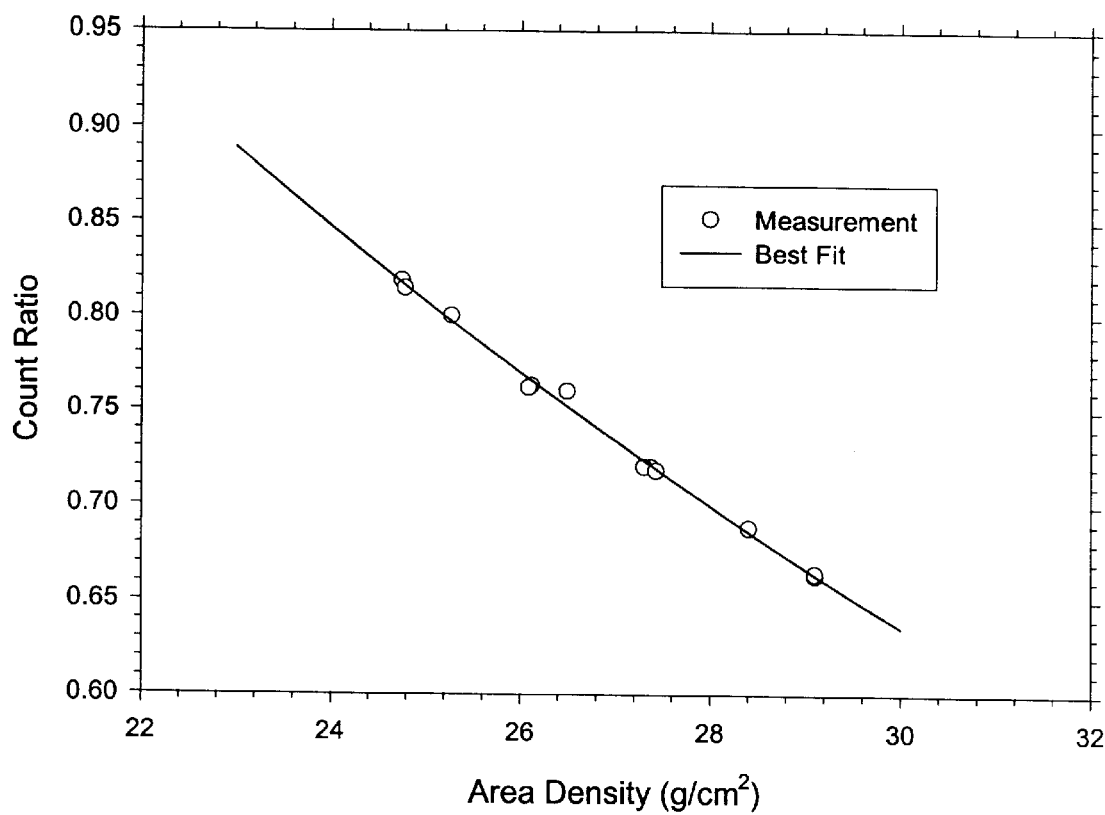
Figure 5 Calibration Curve

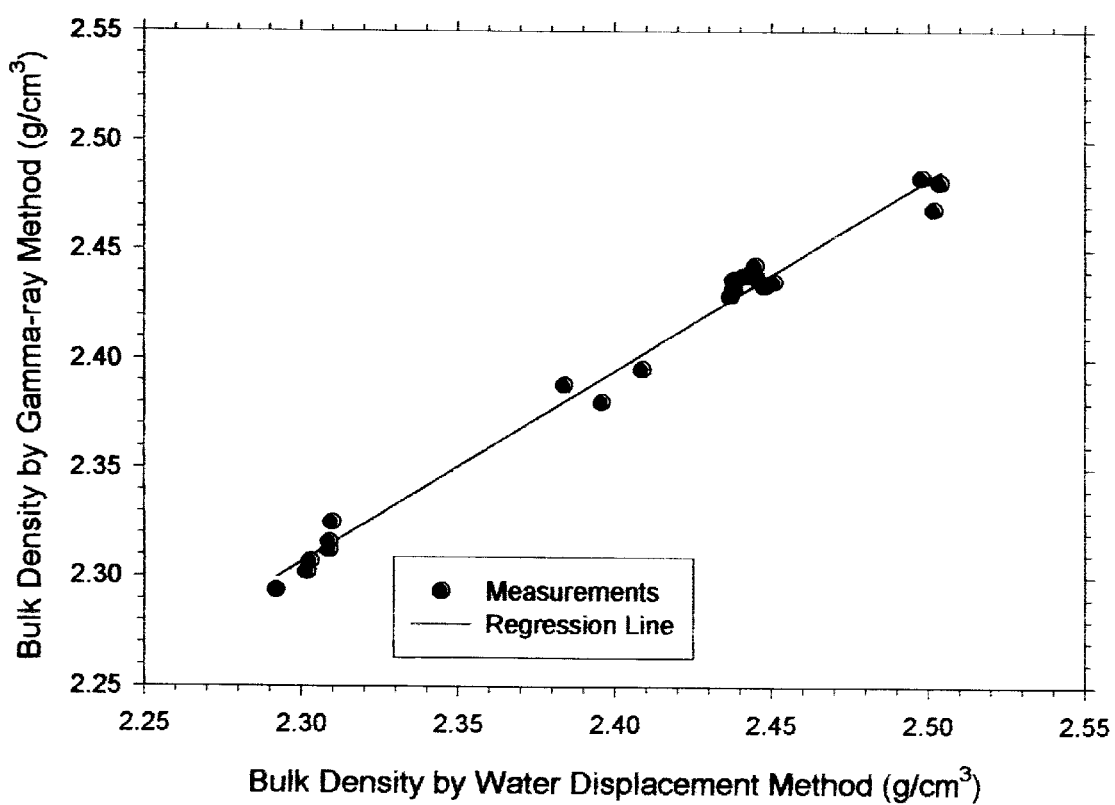
Figure 6 Bulk Density of Unknown Samples

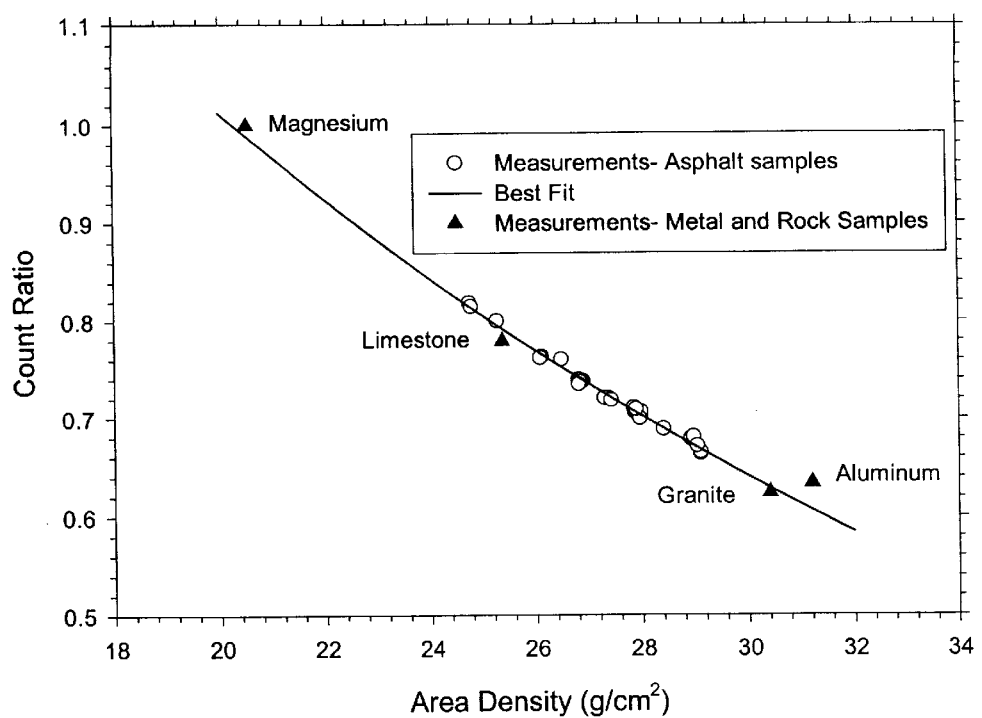
Figure 7 Asphalt Equivalent Nomalization Factors for Metal and Rock Samples

US 6,492,641 B1

APPARATUS AND METHOD FOR GAMMA-RAY DETERMINATION OF BULK DENSITY OF SAMPLES

FIELD OF THE INVENTION

This invention relates to the measurement of bulk density, and more particularly to an apparatus and method for measuring the bulk density of a sample using gamma radiation. The invention is especially suited for measuring the bulk density of relatively small "finite volume" samples, and in particular, cylindrically shaped samples such as core samples or gyratory compacted specimens of asphalt paving material.

BACKGROUND OF THE INVENTION

In the asphalt pavement construction industry, the cylinder is a common sample geometry. In laboratories, cylindrical samples are prepared, typically with a gyratory compactor, and various material properties are studied to determine the best mix design for a pavement. In the field, cylindrical samples are cored from test strips, newly constructed roads, or existing roads. The material properties of these samples are then used to evaluate whether the test strip or the new pavement meets the design criteria and whether the existing road is in good operating condition or in need of repairs. Among the material properties studied in the cylindrical asphalt samples, material bulk density or bulk specific gravity is an important property.

Currently, several methods are used for measuring the density of cylindrical samples: dimensional analysis, the water displacement method, the paraffin coated method, and the para-film-covered method. In each case, the bulk density of a sample is derived by, as in the definition, dividing the dry sample mass by the estimated sample volume. All methods require a balance with a sensitivity of 0.1 g. to measure the mass of the sample. In the dimensional analysis method, sample volume is determined from the radius and thickness (height) measurements. Here, many readings of the radius and thickness of the sample are made using a vernier caliper. The average values of the radius and the thickness are then used to calculate the sample volume. The other methods use the Archimedes Principle for determining the sample volume. These methods require a large container filled with clean water. The water,temperature should be monitored and controlled at a specific temperature, e.g. at 25° C. At one stage of the test, the sample is kept immersed in water for approximately 4 minutes and the weight of the sample, while suspended in water, is recorded. In the "paraffin-coated" method, after determining the dry weight of the sample, a thin coating of paraffin is applied to cover the entire surface area of the sample. Then, the sample is weighed again in air. Finally, the sample is weighed while immersed in water. The "parafilm-covered" method is similar to the "paraffin-coated" method, except that a film is used to wrap the sample. The water displacement test, which is the fastest of all three Archimedes methods, takes about 6 minutes. The single operator precision of the water displacement method is 0.0124 g/cm$^3$ and the paraffin-coated method is less than 0.02 g/cm$^3$. More details can be found in standards ASTM D 2726 for the water displacement method and ASTM D 1188 for the paraffin-coated method.

Because an asphalt mix is heterogeneous and granular in nature, there is no single density determination method to cover all mix designs. The decision on which density determination method to use depends on the aggregate size and whether it is an open or closed mix design. For example, for mixes using aggregate with a nominal aggregate size of 9.5 mm and a void content less than about 6%, the water displacement method provides reasonably accurate densities. For open-graded mixes with larger aggregates and coarser gradations, the water displacement method provides densities higher than the "true" densities. For such samples, the industry recommends using paraffin-coated or para-film covered methods for density determination. However, paraffin-coated and para-film methods are time consuming and their accuracy of density determination have been found to be highly user dependent. Furthermore, for many mix designs, the dimensional analysis method overestimates the volume and yields lower density values than the other methods. However, literature has shown that dimensional analysis provides better estimates of the densities of highly permeable specimens.

With more and more roads being constructed using mixes of large aggregate sizes and/or open graded mix designs, there is a need for developing techniques for determining the density of cylindrical asphalt samples.

For many decades, gamma-ray based nuclear gauges have been successfully used to determine densities of asphalt pavements. This type of gauge provides a non-destructive test method and provides density measurements rapidly (e.g. within 1 to 4 minutes).

Various designs for gamma-ray based surface gauges, depth probes, and the like have been reported in literature and are available commercially. Single system surface density gauges, such as the Model 3400 series Surface Moisture-Density gauges available from applicant's assignee, Troxler Electronic Laboratories, Inc., are designed to be placed on a surface, such as an asphalt pavement surface, and the density determination assumes a sample of relative large or "infinite volume" in relation to the field of view of the gauge. Such gauges are not designed to reliably measure the bulk density of relatively small, "finite volume" samples, such as cylindrically shaped samples of asphalt paving mix.

In commonly owned U.S. Pat. No. 5,151,601, a system is described by which a nuclear asphalt content gauge, such as the Troxler 3200 series asphalt content gauge, can be used to determine the asphalt content of cylindrical samples of asphalt paving mix. However, currently no commercial nuclear gauge is available in the market for determining the density of cylindrical specimens.

SUMMARY OF THE INVENTION

The present invention provides a nuclear density test instrument and method which is suited for measuring the bulk density of relatively small, "finite volume" samples, and is particularly suited for measuring the bulk density of cylindrical specimens, such as cylindrical core samples or gyratory compacted specimens of asphalt paving mix.

In one embodiment, the density gauge of the present invention comprises a plurality of sources of gamma radiation positioned in spaced-apart relation from one another for emitting gamma radiation from a plurality of spaced-apart locations into a sample placed nearby and a detector mounted for receiving gamma radiation which has penetrated the sample. Means is provided cooperating with the detector for calculating the bulk density of the sample based upon the gamma radiation counts by the detector. In one embodiment, each of the sources of gamma radiation is preferably a point source, and the sources are preferably mounted to a source plate. The sources are preferably at least three in number and are arranged in a common plane. In a further more specific aspect, the gauge includes a sample holder configured to hold a cylindrically shaped sample, the sample holder being mounted adjacent to said source plate to orient the sources at spaced locations opposite a first end of the cylindrically shaped sample.

Preferably, the detector is an energy selective detector configured to detect gamma radiation in a predetermined energy spectrum, which desirably is within the range of from 0.1 MeV to 2 MeV. The detector may comprise a scintillation detector, and the system may include an analyzer connected to the scintillation detector for detecting gamma radiation in the desired predetermined energy spectrum. In one specific embodiment, each of the sources is a $^{137}$Cs gamma-ray source with a 0.662 MeV primary energy, and the predetermined energy spectrum measured by the gauge falls within the range of 0.25 to 0.73 MeV.

BRIEF DESCRIPTION OF THE DRAWINGS

Some of the features and advantages of the invention having been described, others will become apparent from the detailed description which follows, and from the accompanying drawings, in which:

FIG. 4 is a chart showing a stabilization spectrum;

FIG. 5 is a density calibration curve graph;

FIG. 6 is a graph comparing the densities determined by the gamma-ray method with densities obtained by the water displacement method; and FIG. 7 is a graph showing measured asphalt equivalent normalization factors for metal and rocks.

DETAILED DESCRIPTION OF THE INVENTION

Figure 1:
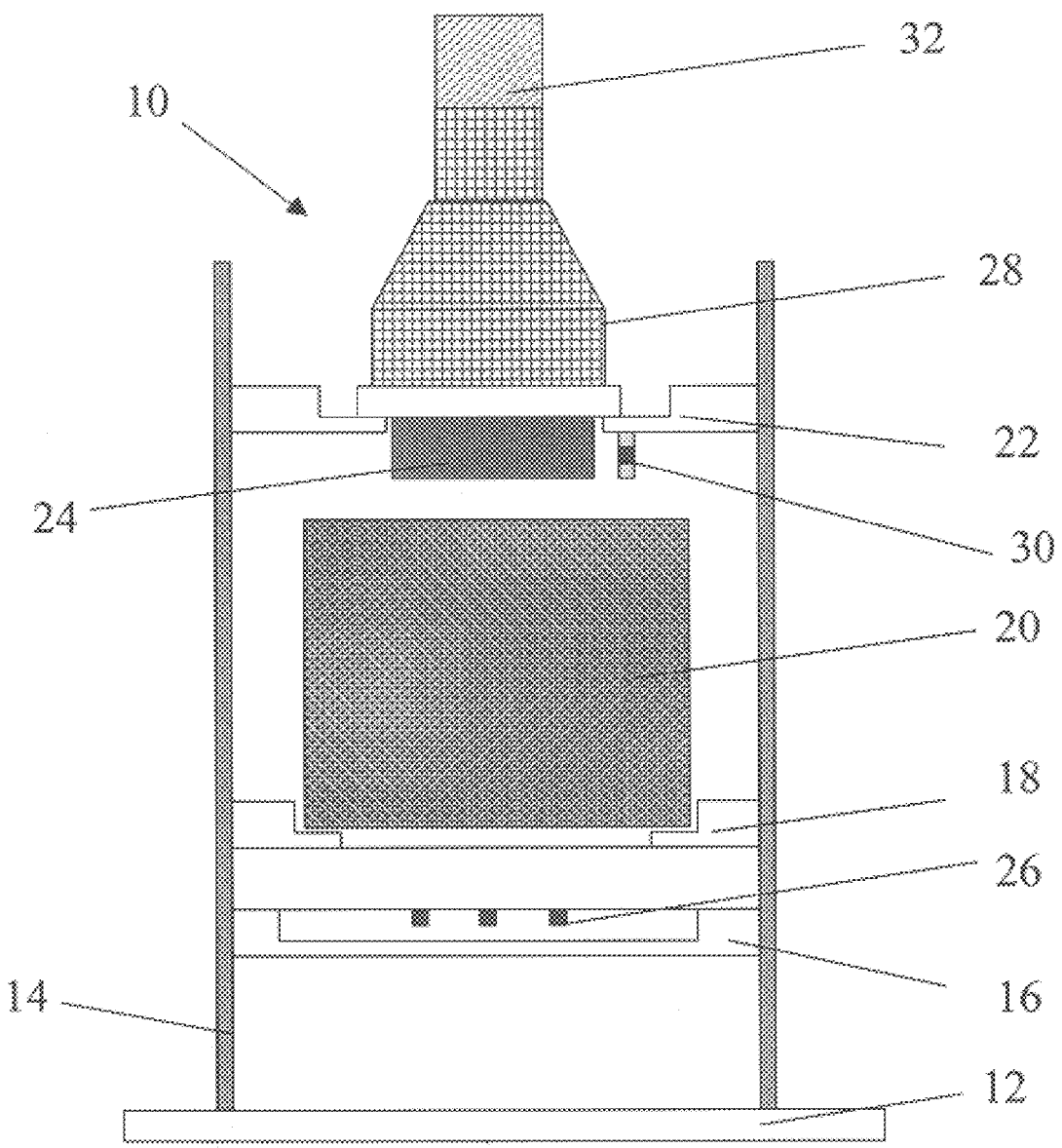
FIG. 1 is a schematic elevational view of a gauge in accordance with an embodiment of the invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Principle

The present invention is based on the scattering and absorption properties of gamma-rays with matter. For gamma-rays with energies less than 2 MeV, there are two dominant interacting mechanisms with matter. In the 0.1 to 2 MeV energy range, the dominant mechanism is inelastic scattering (Compton scattering). For energies less than 0.1 MeV, the dominant mechanism is photoelectric absorption. In the 0.1 to 2 MeV energy range, the amount of gamma-ray scattering (energy degradation) is a function of electronic density of the material and hence a fundamental measurement property. This results in a nuclear attenuation per unit length-mass density. As a consequence, one can see that the actual volume of a homogeneous sample is not as critical as it is in the volumetric based system. This leads to bulk density measurements which are not so affected by the surface properties or texture of a sample. At energies below 0.1 MeV, the photoelectric absorption of gamma-rays is sensitive to the atomic number of the material and hence to the chemical (elemental) composition of the material. Therefore, when a gamma-ray source of sufficient energy is placed near a material, and an energy selective gamma-ray detector is used for gamma-ray detection, gamma-rays mainly undergoing Compton scattering can be counted exclusively. With proper calibration, the gamma-ray count can be converted to an absolute density. Also, the unscattered gamma-rays can be counted which is again a function of the material bulk density According to one specific embodiment of the invention, a $^{137}$Cs gamma-ray source with a 0.662 MeV primary energy is used. However, other gamma-ray sources with different primary energy levels could be employed, such as $^{60}$Co for example. Gamma-rays interacting with the sample are detected with a detector, which is preferably an energy selective detector configured to detect gamma radiation in a predetermined energy spectrum. Gamma radiation detectors may be configured in various ways to be selective to a desired energy spectrum. For example, one may use conventional Geiger-Mueller detector tubes with an appropriate filter, such as cadmium, to filter out low energy gamma radiation. In the embodiment shown and described herein, an energy selective scintillation detector is used, specifically a NaI crystal mounted on a photo-multiplier tube (PMT). Specifically, when using a $^{137}$Cs source, gamma-rays interacting with or passing through the sample with energies in the range 0.25 to 0.73 MeV are counted. Since these gamma-rays contain Compton scattered gamma-rays and unscattered gamma-rays, the count received by a gamma-ray detector resulting from interactions with the material is a good indicator of the material bulk density. The technique uses 0.25 MeV as the low energy limit for selecting the gamma-rays. This energy selection avoids counting gamma-rays with energies which depend on the chemical composition of the material. Hence, the chemical composition error is minimized. The upper limit of 0.73 MeV is selected to include substantially all of the gamma-rays with the characteristic 0.662 MeV primary energy. The gaussian distribution for the 0.662 MeV peak has its upper base at approximately 0.73 MeV because of the finite resolution of the detector. For gamma-ray sources other than $^{137}$Cs, the upper limit would be selected in a similar manner based upon the energy distribution for the particular source selected.

According to the present invention, the source-sample-detector configuration is designed to give the best density estimate of a heterogeneous and granular sample. Since point densities of such samples show a distribution of densities, a large sample volume should be used for estimating the bulk density. Since a cylindrical sample of asphalt mix is of relatively small size (or of "finite volume"), it is desired that the probing particles, which are in this case photons (gamma-rays) should traverse the sample to the fullest extent possible, thereby interacting with and sampling a large portion of the limited size sample. To this end, a plurality of spaced apart point-gamma-ray sources are used. In the illustrated embodiment, five separate sources are used and they are arranged on a plate so as to cover a volume generally corresponding to the size of the sample. In the embodiment shown, which is designed to measure a cylindrical shaped asphalt sample, the five sources are arranged such that the gamma-rays traverse directly along several paths through a large portion of the sample volume. To cover the remaining volume not traversed by the direct gamma-rays, the detector counts gamma-rays with energies less than 0.662 MeV. These energy gamma-rays are the result of multiple scattering in the sample, and have thus filled the entire sample volume.

Apparatus

One embodiment of the gauge is shown in FIG. 1. This embodiment is designed to operate in the direct transmission mode. The gauge is indicated generally by the reference character 10. The gauge includes a base 12, with a plurality of upright support rods 14 projecting upwardly therefrom. A source plate 16 in the form of a circular disc is supported by the support rods 14. A sample holder 18, configured to receive and hold a test sample 20, is mounted to the support rods 14 just above the source plate 16. In the illustrated embodiment, the test sample is formed of asphalt paving mix compacted in the configuration of a right circular cylinder and the sample holder has a circular flange of a diameter adapted to receive and support one of the flat circular ends of the cylindrical sample. A detector support plate 22, mounted to the support rods 14, suspends a sodium iodide scintillation detector 24 just above the upper flat circular end of the sample 20. Thus, the sample 20 is located between the gamma-ray source and the gamma-ray detector.

Figure 2:
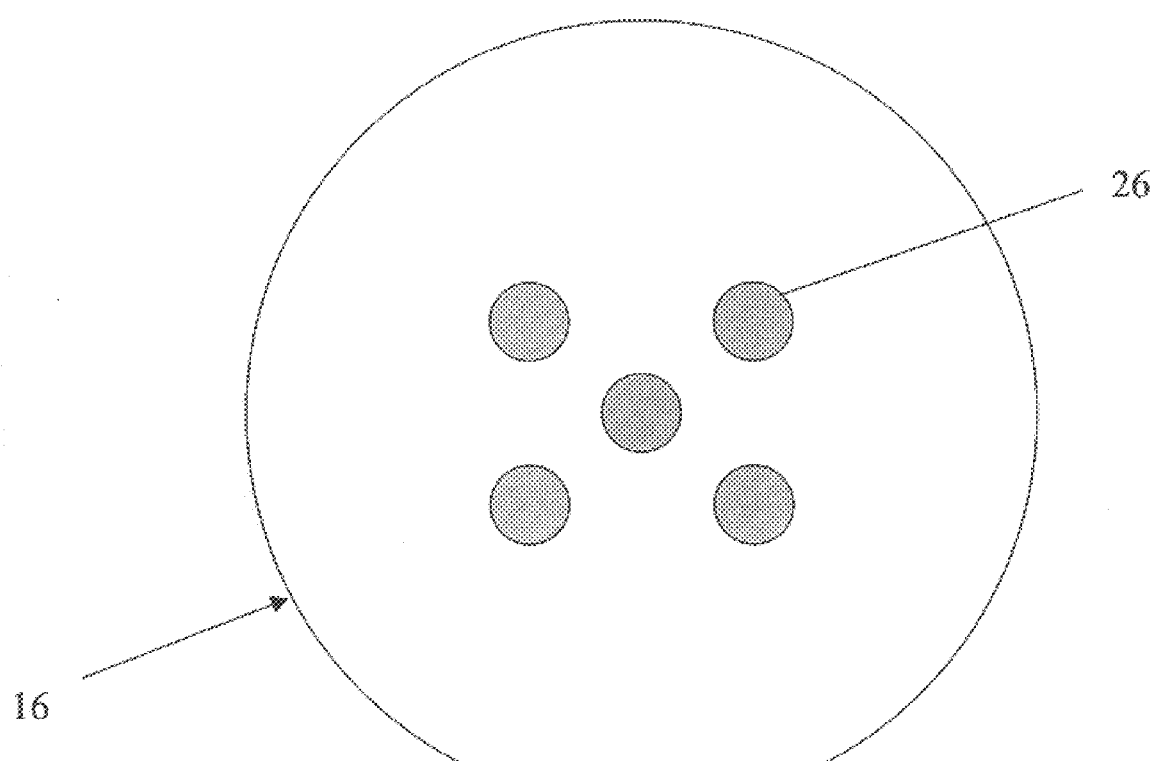
FIG. 2 is a top plan view of a source plate for the gauge, shown with five 10 $\mu$Curie$^{137}$Cs sources.
Figure 3:
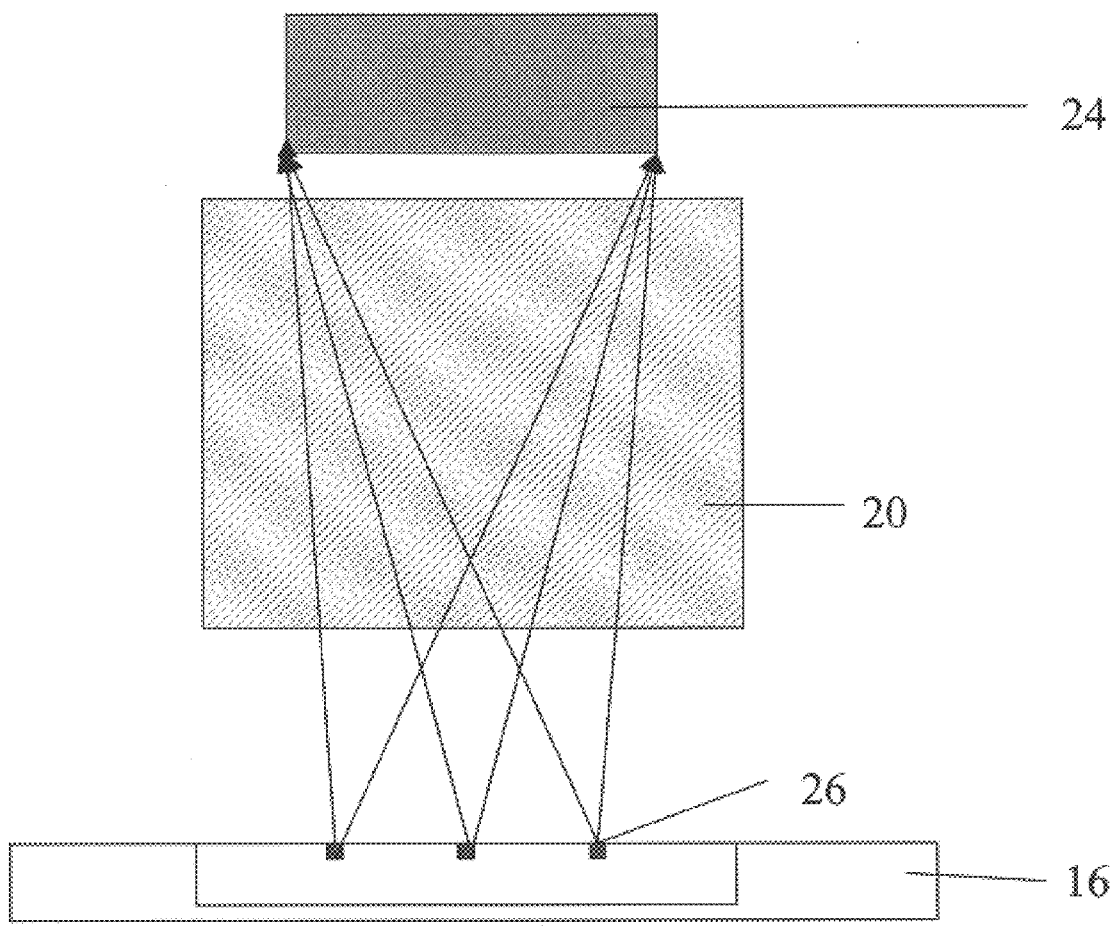
FIG. 3 is a ray diagram showing the path of the gamma rays from the five source locations through the sample volume to the detector, with the path of unscattered gamma-rays shown in solid lines and the path of scattered gamma-rays shown in dotted lines.

As best seen in FIGS. 2 and 3, the source plate 16 contains five 10$\mu$Curie $^{137}$Cs sources 26 located in recesses or wells formed in the source plate. The $^{137}$Cs sources may be in the form of pellets of relatively small size in relation to the overall size of the apparatus, and may thus be considered as "point sources". Alternatively, it may be desirable to fabricate the sources so that they occupy a somewhat larger surface area in relation to their thickness, to thereby increase the interaction of the gamma-rays with the sample. In any event, the location of each source in the source plate is selected such that the direct path of a gamma-ray from the sources to the detector traverses a large portion of the volume of the sample, as may be seen from the ray diagram of FIG. 3. The gamma-ray detector is a NaI crystal mounted on a photo-multiplier tube (PMT) 28. The detector system is held by detector-support-plate 22. The embodiment shown has a sample holder that can accomodate a 150 mm diameter by 110 mm thick cylindrical sample with the cylinder axis in a vertical direction. The apparatus is designed such that the distance between the source plate and the detector support plate can be varied, if necessary. The gauge also has another 1 $\mu$Curie $^{124}$Am gamma-ray source 30 mounted near the detector for spectrum stabilization.

The NaI/PMT detector system is available commercially from Rexon Components, Inc., of Beachwood, Ohio. A high voltage power supply, preamplifier, amplifier, analog-to-digital converter, digital spectrum stabilizer and multi-channel analyzer (MCA), which are available from manufacturers such as Canberra Industries, Inc., Meriden, Conn., and EG&G ORTEC, Oak Ridge, Tenn., receive and process the signals from the detector system. The MCA is a computer card that can be installed on a regular personal computer running a Microsoft operating system.

Spectrum Stabilization

Scintillation detectors are sensitive to temperature fluctuations. In the digital spectrum produced by the MCA (see FIG. 4), the x-axis represents the energy of a gamma-ray and y-axis represents the counts corresponding to a particular gamma-ray energy. When the temperature fluctuates, the spectrum fluctuates in the x-direction. Therefore, a peak once centered on one channel may end up centered on a different channel. If one wants to find the number of gamma-rays with energies between $E_{lower}$ and $E_{upper}$, because of these fluctuations, the counts obtained from using the "normal" spectrum will have large uncertainties. This uncertainty is due to the temperature sensitivity. The digital spectrum stabilizer is used to stabilize the spectral drifts resulting from temperature fluctuations in the NaI detector. Two gamma-ray peaks are used for the spectrum stabilization—a 0.056 MeV peak from a 1 $\mu$Curie $^{241}$Am source placed near the detector and the 0.662 MeV peak from the 50 $\mu$Curie $^{137}$Cs sources in the source plate.

During a 4 minute counting time, the MCA collects counts in 1-minute increments. Each 1-minute spectrum is then corrected for signal amplitude fluctuations and stored in a buffer. At the end of counting, the MCA gives two spectra—a normal spectrum, which is a spectrum collected without signal amplitude adjustments, and a stabilized spectrum, which is constructed using corrected 1-minute spectra in the buffer. FIG. 4 shows an example of a normal spectrum and a stabilized spectrum for a Magnesium cylinder. Note that the centroid of the 0.056 MeV peak in the normal spectrum is in channel number 23 and the same in the stabilized spectrum is in channel number 19. In the normal spectrum, depending on the ambient temperature, the centroid can drift from channel to channel. However, when the digital spectrum stabilizer is used, the centroid will be always brought to channel number 19. This correction is applied across the entire spectrum. During a 48 hour test period, the stabilizer maintained the centroid of the 0.662 MeV $^{137}$Cs peak within ±0.075 channel numbers (1-sigma).

Calibration Method

As with other nuclear gauges, the gauge has to be calibrated to convert gamma-ray counts to material bulk densities. Preliminary calibration was performed using magnesium and aluminum metal cylinders and an asphalt cylinder. When obtaining counts from spectra, gamma-rays with energies from 0.250 to 0.730 MeV were counted. For a 10-minute count, the precision of density measurement was found to be 0.0015 g/cm$^3$ at 2.35 g/cm$^3$ (1-sigma). For a 4-minute count, at the same density, the precision lowered to about 0.0045 g/Cm$^3$ (1-sigma). Note that 1 lb/ft$^3$ (PCF)= 0.01602 g/cm$^3$. The density determined by the method was found to be independent of the sample orientation. Such orientations are 1) a rotation about a vertical axis through the center of the sample holder, and 2) placing the sample on the sample holder with face up or down.

The gauge was used to determine the densities of several samples. Samples were placed on the holder in a random orientation with the cylinder axis near the vertical line passing through the center of the sample holder. For each sample, several measurements were made on different days. Using the same calibration, the density was determined for 10-minute counts (Table 1). The measurement repeatability for 10-minute counts was about 0.002 g/cm$^3$ (1-sigma).

Twelve asphalt cylinders (Table 2, sample numbers 1 to 12) were used to calibrate the prototype gauge. All samples were 150 mm diameter by 115 mm high cylindrical samples with North Carolina granite as the aggregate type with nominal sizes 9.5 mm and 12.5 mm. Densities of all samples were determined by the water displacement method ($G_{mb}$). Heights of the samples were measured using a vernier caliper. The background radiation from the sample and its surrounding was measured by taking counts when the five point $^{137}$Cs gamma-ray sources were not present in the source holder. An average value of the background in the energy interval from 0.25 to 0.73 MeV was used to determine the true gamma-ray count at the detector from the five point $^{137}$Cs sources. Some properties of the samples are given in Table 2. The count ratio (CR) for each sample was determined by $$CR = \frac{(Cnt - Bgd)}{Std}$$

Where

Cnt=10-minute gamma-ray count,

Bgd=10-minute average background count, and

Std=10-minute gamma-ray count for Magnesium cylinder minus Bgd.

FIG. 5 shows the count ratio (CR) vs. area density (D') for all samples. Here, $$D'=G_{mb}h$$

Here, h is the height of the cylinder. The curve in FIG. 5 is the best fit to data of the form $$CR=Ae^{-BD'}-C$$

Where A, B, and C are the fitting coefficients or calibration constants. The best fit gave the following values for the three calibration constants.

A=2.6750

B=0.04790 cm$^2$/g, and

C=6.36 E-10.

The coefficient of determination, R$^2$, for the fit is 0.996.

Using the density calibration, bulk densities of twenty-one unknown asphalt cylinders were measured (Table 2, sample numbers 13 to 33). The densities were calculated using the calibration constants A, B, and C, the standard count Std, the average background count Bgd, the height of the cylinder h, and the count ratio CR. The density D is given by $$D = \frac{-1}{Bh}\text{Ln}\left(\frac{CR+C}{A}\right)$$

Then, the densities of all samples were determined by the water displacement method ($G_{mb}$).

FIG. 6 shows a comparison between the densities of unknown asphalt samples determined by the water displacement method and by the gamma-ray method. The line in this figure is the regression line with an R$^2$ of 0.988. The density differences for all samples (listed in the column labeled $G_{mb}$–D) are shown in Table 3. The density difference for asphalt samples were –0.006±0.011 g/cm$^3$ (1-sigma) with a minimum difference of –0.015 g/cm$^3$ and a maximum difference of 0.033 g/cm$^3$.

All asphalt cylinders, cylinders used for calibration and cylinders used as unknowns, were then used to determine the calibration coefficients for asphalt mixes made with granite-type aggregates (FIG. 7). Based on this best curve, calculations were made of the normalization factors for converting gravimetric densities to "asphalt equivalent" densities for metal and rock samples. These factors are given in Table 4 together with the normalization factors that Troxler nuclear surface gauges routinely use.

When calibrating the gauge, one can then use three metal or rock cylinders with 'asphalt equivalent' densities instead of a large number of cylinders made with real asphalt mixes.

TABLE 1

Repeatability of sample counts and densities

| Sample | 01/03/00 | 01/05/00 | 01/11/00 | 01/13/00 |
|---|---|---|---|---|
| Mg (1762 kg/m$^3$) | 1761 | 1765 | 1763 | 1767 |
|  | 1762 |  | 1762 | 1768 |
|  |  |  |  | 1763 |
|  |  |  |  | 1768 |
| Al (2574 kg/m$^3$) | 2573 | 2575 | 2575 | 2578 |
|  | 2576 |  | 2574 | 2578 |
| RT-03-01 | 2141 | 2139 | 2141 | 2143 |
| (2141 kg/m$^3$) |  |  | 2143 | 2145 |
| BAZ-01-01 | 2463 | 2463 | NA | NA |
| (2487 kg/m$^3$) |  |  |  |  |
| CAY-09-01 | NA | NA | 2458 | 2463 |
| (2451 kg/m$^3$) |  |  | 2461 | 2458 |

NA -- Not Available

TABLE 2

| Sample Number | Sample I.D. | Diameter (in) | Height (in) | M/V (g/cm$^2$) | Gmb (g/cm$^2$) | Size | AC (%) | Gmm (g/cm$^2$) |
|---|---|---|---|---|---|---|---|---|
| 1 | RT-01-01 | 5.911 | 4.575 | 2.342 | 2.357 | RI-2 9.5 mm | 6.3 | 2.409 |
| 2 | RT-01-02 | 5.911 | 4.573 | 2.343 | 2.359 | RI-2 9.5 mm | 6.3 | 2.409 |
| 3 | RT-02-01 | 5.913 | 4.549 | 2.234 | 2.259 | RI-2 9.5 mm | 6.3 | 2.409 |
| 4 | RT-02-02 | 5.906 | 4.550 | 2.238 | 2.261 | RI-2 9.5 mm | 6.3 | 2.409 |
| 5 | RT-03-01 | 5.914 | 4.551 | 2.113 | 2.141 | RI-2 9.5 mm | 6.3 | 2.409 |
| 6 | RT-03-02 | 5.916 | 4.544 | 2.115 | 2.143 | RI-2 9.5 mm | 6.3 | 2.409 |
| 7 | BAZ-01-01 | 5.908 | 4.496 | 2.454 | 2.487 | SP 9.5 mm | 5.4 | 2.531 |
| 8 | BAZ-02-01 | 5.906 | 4.497 | 2.357 | 2.401 | SP 9.5 mm | 5.4 | 2.531 |
| 9 | BAZ-03-02 | 5.907 | 4.528 | 2.240 | 2.303 | SP 9.5 mm | 5.4 | 2.531 |
| 10 | BAZ-04-01 | 5.930 | 4.486 | 2.146 | 2.218 | SP 9.5 mm | 5.4 | 2.531 |
| 11 | H-1 | 5.910 | 4.534 | 2.476 | 2.527 | SP 12.5 mm | 5.2 | 2.593 |
| 12 | H-2 | 5.912 | 4.537 | 2.471 | 2.525 | SP 12.5 mm | 5.2 | 2.593 |
| 13 | CAY-08-04 | 5.914 | 4.584 | 2.352 | 2.448 | CCM 9.5 mm | 5.4 | 2.531 |
| 14 | CAY-08-05 | 5.912 | 4.582 | 2.354 | 2.451 | CCM 9.5 mm | 5.4 | 2.531 |
| 15 | CAY-08-06 | 5.901 | 4.501 | 2.408 | 2.445 | CCM 9.5 mm | 5.4 | 2.531 |
| 16 | CAY-09-01 | 5.913 | 4.546 | 2.445 | 2.504 | CCM 19.0 mm | 4.5 | 2.597 |
| 17 | CAY-09-02 | N/A | 4.558 | N/A | 2.502 | CCM 19.0 mm | 4.5 | 2.597 |
| 18 | CAY-09-03 | N/A | 4.576 | N/A | 2.498 | CCM 19.0 mm | 4.5 | 2.597 |
| 19 | 759-05 | N/A | 4.599 | N/A | 2.302 | RI-2 9.5 mm | 6.3 | 2.409 |
| 20 | 759-07 | N/A | 4.606 | N/A | 2.292 | RI-2 9.5 mm | 6.3 | 2.409 |

TABLE 2-continued

| Sample Number | Sample I.D. | Diameter (in) | Height (in) | M/V (g/cm$^2$) | Gmb (g/cm$^2$) | Size | AC (%) | Gmm (g/cm$^2$) |
|---|---|---|---|---|---|---|---|---|
| 21 | 759-08 | N/A | 4.583 | N/A | 2.303 | RI-2 9.5 mm | 6.3 | 2.409 |
| 22 | 771-01 | N/A | 4.512 | N/A | 2.441 | CCM 9.5 mm | 5.4 | 2.531 |
| 23 | 771-03 | N/A | 4.490 | N/A | 2.445 | CCM 9.5 mm | 5.4 | 2.531 |
| 24 | 771-04 | N/A | 4.514 | N/A | 2.438 | CCM 9.5 mm | 5.4 | 2.531 |
| 25 | 772-01 | N/A | 4.508 | N/A | 2.437 | CCM 9.5 mm | 5.4 | 2.531 |
| 26 | 772-02 | N/A | 4.489 | N/A | 2.444 | CCM 9.5 mm | 5.4 | 2.531 |
| 27 | 772-03 | N/A | 4.503 | N/A | 2.438 | CCM 9.5 mm | 5.4 | 2.531 |
| 28 | 223-02 | N/A | 4.598 | N/A | 2.396 | CCM 9.5 mm | 5.4 | 2.531 |
| 29 | 223-03 | N/A | 4.617 | N/A | 2.384 | CCM 9.5 mm | 5.4 | 2.531 |
| 30 | 223-04 | N/A | 4.558 | N/A | 2.409 | CCM 9.5 mm | 5.4 | 2.531 |
| 31 | 746-01 | N/A | 4.582 | N/A | 2.309 | RI-2 9.5 mm | 6.3 | 2.409 |
| 32 | 746-02 | 6.011 | 4.576 | 1.762 | 2.309 | RI-2 9.5 mm | 6.3 | 2.409 |
| 33 | 746-03 | N/A | 4.570 | N/A | 2.310 | RI-2 9.5 mm | 6.3 | 2.409 |

NA - Not Available

TABLE 3

Comparison of Densities Determined by the Invention to that by the Water Displacement Method

| Sample Number | Sample I.D. | G$_{mb}$ (g/cm$^2$) | Height (in) | Count (10 min) | Bgd (10 min) | Net Count (10 min) | Ratio | D (g/cm$^2$) | G$_{mb}$-D (kg/m$^3$) |
|---|---|---|---|---|---|---|---|---|---|
| 1 | RT-01-01 | 2.355 | 4.575 | 1743280 | 64000 | 1679280 | 0.720 | 2.358 | -2.6 |
| 2 | RT-01-02 | 2.35 | 4.573 | 1743317 | 64000 | 1679317 | 0.720 | 2.359 | -8.6 |
| 3 | RT-02-01 | 2.26 | 4.549 | 1843631 | 64000 | 1779631 | 0.763 | 2.266 | -6.2 |
| 4 | RT-02-02 | 2.257 | 4.55 | 1840810 | 64000 | 1776810 | 0.762 | 2.269 | -11.5 |
| 5 | RT-03-01 | 2.141 | 4.551 | 1973188 | 64000 | 1909188 | 0.819 | 2.138 | 2.7 |
| 6 | RT-03-02 | 2.147 | 4.544 | 1963662 | 64000 | 1899662 | 0.815 | 2.151 | -3.6 |
| 7 | BAZ-01-01 | 2.487 | 4.496 | 1669048 | 64000 | 1605048 | 0.688 | 2.482 | 5.4 |
| 8 | BAZ-02-02 | 2.401 | 4.497 | 1738441 | 64000 | 1674441 | 0.718 | 2.404 | -2.7 |
| 9 | BAZ-03-02 | 2.303 | 4.528 | 1836585 | 64000 | 1772585 | 0.760 | 2.284 | 19.1 |
| 10 | BAZ-04-01 | 2.218 | 4.486 | 1930013 | 64000 | 1866013 | 0.800 | 2.211 | 6.8 |
| 11 | H-1 | 2.527 | 4.534 | 1610913 | 64000 | 1546913 | 0.663 | 2.528 | -0.7 |
| 12 | H-2 | 2.525 | 4.537 | 1613565 | 64000 | 1549565 | 0.664 | 2.523 | 2.1 |
| 13 | CAY-08-04 | 2.448 | 4.478 | 1720589 | 64000 | 1656589 | 0.710 | 2.434 | 14.4 |
| 14 | CAY-08-05 | 2.451 | 4.474 | 1720816 | 64000 | 1656816 | 0.710 | 2.436 | 15.5 |
| 15 | CAY-08-06 | 2.445 | 4.501 | 1700748 | 64000 | 1636748 | 0.702 | 2.443 | 1.8 |
| 16 | CAY-09-01 | 2.504 | 4.546 | 1645141 | 64000 | 1581141 | 0.678 | 2.481 | 22.5 |
| 17 | CAY-09-02 | 2.502 | 4.558 | 1650293 | 64000 | 1586293 | 0.680 | 2.469 | 32.9 |
| 18 | CAY-09-03 | 2.498 | 4.576 | 1628947 | 64000 | 1564947 | 0.671 | 2.484 | 14.3 |
| 19 | 759-05 | 2.302 | 4.599 | 1784293 | 64000 | 1720293 | 0.738 | 2.302 | -0.1 |
| 20 | 759-07 | 2.292 | 4.606 | 1788908 | 64000 | 1724908 | 0.740 | 2.294 | -1.9 |
| 21 | 759-08 | 2.303 | 4.583 | 1787279 | 64000 | 1723279 | 0.739 | 2.307 | -4.1 |
| 22 | 771-01 | 2.441 | 4.512 | 1699848 | 64000 | 1635848 | 0.701 | 2.438 | 2.8 |
| 23 | 771-03 | 2.445 | 4.49 | 1710575 | 64000 | 1646575 | 0.706 | 2.438 | 6.8 |
| 24 | 771-04 | 2.438 | 4.514 | 1700193 | 64000 | 1636193 | 0.702 | 2.437 | 1.2 |
| 25 | 772-01 | 2.437 | 4.508 | 1709851 | 64000 | 1645851 | 0.706 | 2.429 | 7.7 |
| 26 | 772-02 | 2.444 | 4.489 | 1709257 | 64000 | 1645257 | 0.705 | 2.440 | 3.8 |
| 27 | 772-03 | 2.438 | 4.503 | 1709436 | 64000 | 1645436 | 0.706 | 2.432 | 5.6 |
| 28 | 223-02 | 2.396 | 4.598 | 1710967 | 64000 | 1646967 | 0.706 | 2.381 | 15.5 |
| 29 | 223-03 | 2.384 | 4.617 | 1694632 | 64000 | 1630632 | 0.699 | 2.388 | -4.5 |
| 30 | 223-04 | 2.409 | 4.558 | 1716174 | 64000 | 1652174 | 0.708 | 2.396 | 13.3 |
| 31 | 746-01 | 2.309 | 4.582 | 1782925 | 64000 | 1718925 | 0.737 | 2.312 | -3.1 |
| 32 | 746-02 | 2.309 | 4.576 | 1781946 | 64000 | 1717946 | 0.737 | 2.316 | -7.2 |
| 33 | 746-03 | 2.31 | 4.57 | 1776317 | 64000 | 1712317 | 0.734 | 2.325 | -15.1 |
| 34 | Mg | 1.784 | 4.531 | 2393211 | 61148 | 2332063 | 1 | 1.762 | 21.6 |
| 35 | Lime | 2.2 | 4.541 | 1877033 | 59481 | 1817552 | 0.779 | 2.229 | -29.5 |
| 36 | Granite | 2.625 | 4.56 | 1536033 | 81564 | 1454469 | 0.624 | 2.639 | -14.5 |
| 37 | Al | 2.713 | 4.528 | 1536514 | 58580 | 1477934 | 0.634 | 2.628 | 85.2 |

Bgd - Background

TABLE 4

Asphalt equivalent density normalization factors

| Sample | Normalization Factor | | |
|---|---|---|---|
| | "Asphalt Cylinder" | "Soil" (for M34XX) | "asphalt" (for M3450 & M4640) |
| Magnesium | 0.9931 | 0.988 | 0.988 |
| Limestone | 1.0142 | 1.01 | — |
| Granite | 1.0022 | 0.99 | — |
| Aluminum | 0.9650 | 0.964 | 0.949 |

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. Apparatus for measuring bulk density of a sample, comprising:
   a plurality of sources of gamma radiation positioned in spaced-apart relation from one another for emitting gamma radiation from a plurality of spaced-apart locations into a sample placed nearby;
   a detector mounted for receiving gamma radiation which has penetrated the sample; and
   means cooperating with said detector for calculating the bulk density of the sample based upon the gamma radiation counts by said detector.

2. Apparatus according to claim 1, wherein each of said sources of gamma radiation is a point source.

3. Apparatus according to claim 1, including a source plate, said sources being mounted to said source plate.

4. Apparatus according to claim 3, wherein said sources are at least three in number and are arranged in a common plane.

5. Apparatus according to claim 4, additionally including a sample holder configured to hold a cylindrically shaped sample, said sample holder being mounted adjacent to said source plate to orient said sources at spaced locations opposite a first surface of the cylindrically shaped sample.

6. Apparatus according to claim 5, wherein said detector is mounted so as to be oriented on the opposite side of the sample from said first surface.

7. Apparatus according to claim 1, wherein said detector is configured to detect gamma radiation in a predetermined energy spectrum.

8. Apparatus according to claim 7, wherein said detector comprises a scintillation detector, and wherein said means for calculating the bulk density of the sample includes an analyzer connected to said scintillation detector for detecting gamma radiation in a predetermined energy spectrum.

9. Apparatus according to claim 7, wherein said predetermined energy spectrum falls within the range of from 0.1 MeV to 2 MeV.

10. Apparatus according to claim 9, wherein each of said sources comprises a $^{137}Cs$ gamma-ray source with a 0.662 MeV primary energy.

11. Apparatus according to claim 10, wherein said predetermined energy spectrum falls within the range of 0.25 to 0.73 MeV.

12. Apparatus for measuring bulk density of a sample, comprising:
   a sample holder;
   a plate mounted in proximity to said sample holder;
   a plurality of sources of gamma radiation located in said plate adjacent said sample holder, said sources being positioned in spaced-apart relation from one another for emitting gamma radiation from a plurality of spaced-apart locations into a sample placed in said sample holder, each of said sources comprising an isotope having a characteristic primary energy;
   a detector mounted for receiving gamma radiation which has penetrated the sample; and
   means cooperating with said detector for calculating the bulk density of the sample based upon the gamma radiation counts by said detector.

13. Apparatus according to claim 12, wherein said sample holder is of a planar, generally circular configuration for receiving a first end of a cylindrically shaped sample.

14. Apparatus according to claim 13, wherein said plate is of a generally circular configuration and is mounted adjacent to said sample holder with said spaced apart sources therein being located opposite said first end of the sample.

15. Apparatus according to claim 14, wherein said detector is mounted so as to be oriented opposite a second end of the cylindrically shaped sample.

16. Apparatus for measuring bulk density of a cylindrically shaped sample, comprising:
   a base;
   a sample holder carried by said base and having a surface configured for receiving and holding a first generally planar end of the cylindrically shaped sample;
   a plate mounted in proximity to said sample holder;
   at least three sources of gamma radiation located in said plate adjacent said sample holder, said sources being positioned in spaced-apart relation from one another for emitting gamma radiation from at least three spaced-apart locations into said one end of the sample, each of said sources comprising an isotope having a characteristic primary energy;
   a detector positioned adjacent a second generally planar end of the cylindrically shaped sample opposite said first end for receiving gamma radiation which has penetrated the sample; and
   means cooperating with said detector for calculating the bulk density of the sample based upon the gamma radiation counts by said detector.

17. Apparatus according to claim 16, wherein said detector comprises a scintillation detector, and wherein said means for calculating the bulk density of the sample includes an analyzer connected to said scintillation detector for detecting gamma radiation in a predetermined energy spectrum.

18. Apparatus according to claim 17, wherein said predetermined energy spectrum falls within the range of 0.1 MeV to 2 MeV.

19. Apparatus according to claim 18, wherein each of said sources comprises a $^{137}Cs$ gamma-ray source with a 0.662 MeV primary energy.

20. Apparatus according to claim 19, wherein said predetermined energy spectrum falls within the range of 0.25 to 0.73 MeV.

21. Apparatus according to claim 17, wherein each of said sources has a radiation activity of no more than 20 microcurie.

22. Apparatus according to claim 17, wherein the total radiation activity of all of said sources does not exceed 10 microcurie.

23. Apparatus according to claim 17, additionally including a digital spectrum stabilizer operable to compensate for spectral drifts in said scintillation detector.

24. Apparatus according to claim 23, wherein said digital spectrum stabilizer includes a reference source of gamma radiation having a characteristic primary energy different from that of said sources and outside of said predetermined energy spectrum.

25. A method for measuring bulk density of a sample, comprising:
   directing gamma radiation into a sample from a plurality of spaced-apart gamma radiation sources;
   detecting gamma radiation which has penetrated the sample; and
   calculating the bulk density of the sample based upon the detected counts of gamma radiation.

26. A method according to claim 25, wherein said step of directing radiation comprises directing gamma radiation from a plurality of point sources.

27. A method according to claim 26, wherein said sources are at least three in number and are arranged in a common plane.

28. A method according to claim 27, wherein said step of directing radiation comprises directing gamma radiation into a first end of a cylindrically shaped sample, and said detecting step comprises detecting radiation at the opposite end of said cylindrically shaped sample.

29. A method according to claim 25, wherein said step of detecting is achieved with a scintillation detector, and wherein said step of calculating the bulk density of the sample is performed by detecting gamma radiation in a predetermined energy spectrum.

30. A method according to claim 29, wherein said step of calculating bulk density comprises calculating the bulk density of the sample based upon the gamma radiation counts in a predetermined energy spectrum falling within the range of from 0.1 MeV to a maximum value corresponding to the base of the characteristic primary energy of said sources.

31. A method according to claim 30, wherein each of said sources comprises a $^{137}$Cs gamma-ray source with a 0.662 MeV primary energy.

32. A method according to claim 31, wherein said predetermined energy spectrum falls within the range of 0.25 to 0.73 MeV.

33. A method according to claim 30, wherein each of said sources has a radiation activity of no more than 20 microcurie.

34. A method according to claim 30, wherein the total radiation activity of all of said sources does not exceed 10 microcurie.

35. A method for measuring bulk density of a cylindrically shaped sample, comprising:
   providing a cylindrically shaped sample having flat, generally circular opposite ends,
   positioning one end of the sample in proximity to at least three sources of gamma radiation, said sources being positioned in spaced-apart relation from one another for emitting gamma radiation from at least three spaced-apart locations into said one end of the sample, each of said sources comprising an isotope having a characteristic primary energy;
   positioning the opposite end of the sample in proximity to a detector for receiving gamma radiation which has penetrated the sample; and
   calculating the bulk density of the sample based upon the gamma radiation counts by said detector.

36. A method according to claim 35, wherein said step of calculating the bulk density of the sample comprises detecting gamma radiation in a predetermined energy spectrum within the range of 0.1 MeV to 2 MeV.

* * * * *